(12) United States Patent
Williams

(10) Patent No.: US 9,987,001 B2
(45) Date of Patent: Jun. 5, 2018

(54) SURGICAL ANASTOMOSIS APPARATUS

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 448 days.

(21) Appl. No.: 14/737,552

(22) Filed: Jun. 12, 2015

(65) Prior Publication Data

US 2016/0361057 A1    Dec. 15, 2016

(51) Int. Cl.
| *A61B 17/068* | (2006.01) |
| *A61B 17/10*  | (2006.01) |
| *A61B 17/115* | (2006.01) |
| *A61B 17/00*  | (2006.01) |

(52) U.S. Cl.
CPC .......... *A61B 17/068* (2013.01); *A61B 17/105* (2013.01); *A61B 17/1155* (2013.01); *A61B 2017/0046* (2013.01); *A61B 2017/00398* (2013.01); *A61B 2017/00473* (2013.01); *A61B 2017/00477* (2013.01)

(58) Field of Classification Search
CPC ................ A61B 17/115; A61B 17/068; A61B 2017/07257
See application file for complete search history.

(56) References Cited

U.S. PATENT DOCUMENTS

| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |

(Continued)

FOREIGN PATENT DOCUMENTS

| CA | 908529 A | 8/1972 |
| DE | 1057729 B | 5/1959 |

(Continued)

OTHER PUBLICATIONS

European Search Report dated Aug. 19, 2016, issued in EP Application No. 16 17 4031.

Primary Examiner — Andrew M Tecco

(57) ABSTRACT

A surgical circular fastener apparatus includes an elongated body defining a longitudinal axis and having proximal and distal ends, a fastener cartridge disposed adjacent the distal end of the body, an anvil retainer releasably mounted relative to the fastener cartridge; and a manually operably release configured to move between a first position corresponding to a secured condition of the anvil retainer relative to the fastener cartridge and a second position corresponding to a release condition of the anvil retainer relative to the fastener cartridge.

16 Claims, 11 Drawing Sheets

(56) References Cited

U.S. PATENT DOCUMENTS

| | | |
|---|---|---|
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicola |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicola |

(56) References Cited

U.S. PATENT DOCUMENTS

| | | |
|---|---|---|
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicola |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |

(56) References Cited

U.S. PATENT DOCUMENTS

| | | |
|---|---|---|
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,708,212 B2 | 4/2014 | Williams |
| 8,709,026 B2 | 4/2014 | Viola |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,770,460 B2 | 7/2014 | Belzer |
| 8,777,082 B2 | 7/2014 | Scirica |
| 8,789,737 B2 | 7/2014 | Hodgkinson et al. |
| 8,801,734 B2 | 8/2014 | Shelton, IV et al. |
| 8,801,735 B2 | 8/2014 | Shelton, IV et al. |
| 8,827,138 B2 | 9/2014 | Smith et al. |
| 8,833,630 B2 | 9/2014 | Milliman |
| 8,840,004 B2 | 9/2014 | Holsten et al. |
| 8,844,791 B2 | 9/2014 | Smith et al. |
| 8,844,792 B2 | 9/2014 | Viola |
| 8,845,662 B2 | 9/2014 | Yamakawa |
| 8,893,948 B2 | 11/2014 | Williams |
| 8,899,466 B2 | 12/2014 | Baxter, III et al. |
| 8,900,255 B2 | 12/2014 | Ecker |
| 8,905,286 B2 | 12/2014 | Kostrzewski |
| 8,905,289 B2 | 12/2014 | Patel et al. |
| 8,910,847 B2 | 12/2014 | Nalagatla et al. |
| 8,911,458 B2 | 12/2014 | Bassan et al. |
| 8,920,444 B2 | 12/2014 | Hiles et al. |
| 8,925,785 B2 | 1/2015 | Holsten et al. |
| 8,925,786 B2 | 1/2015 | Holsten et al. |
| 8,931,680 B2 | 1/2015 | Milliman |
| 8,967,448 B2 | 3/2015 | Carter et al. |
| 8,967,449 B2 | 3/2015 | Viola |
| 8,978,955 B2 | 3/2015 | Aronhalt et al. |
| 8,998,061 B2 | 4/2015 | Williams et al. |
| 9,010,605 B2 | 4/2015 | Olson et al. |
| 9,010,608 B2 | 4/2015 | Casasanta, Jr. et al. |
| 9,010,609 B2 | 4/2015 | Carter et al. |
| 9,010,612 B2 | 4/2015 | Stevenson et al. |
| 9,016,547 B2 | 4/2015 | Mozdzierz et al. |
| 9,022,274 B2 | 5/2015 | Penna |
| 9,038,882 B2 | 5/2015 | Racenet et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2005/0116009 A1* | 6/2005 | Milliman ............ A61B 17/068 227/176.1 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |

(56) References Cited

U.S. PATENT DOCUMENTS

| | | |
|---|---|---|
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 * | 10/2013 | Ma .................... A61B 1/04 227/176.1 |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2013/0334279 A1 | 12/2013 | Prior |
| 2014/0008413 A1 | 1/2014 | Williams |
| 2014/0012317 A1 | 1/2014 | Orban et al. |
| 2014/0021239 A1 | 1/2014 | Kostrzewski |
| 2014/0042206 A1 | 2/2014 | Milliman |
| 2014/0054353 A1 | 2/2014 | Milliman et al. |
| 2014/0054354 A1 | 2/2014 | Holsten et al. |
| 2014/0054356 A1 | 2/2014 | Hartwick et al. |
| 2014/0069983 A1 | 3/2014 | Holsten et al. |
| 2014/0097224 A1 | 4/2014 | Prior |
| 2014/0097225 A1 | 4/2014 | Viola |
| 2014/0097226 A1 | 4/2014 | Williams |
| 2014/0131417 A1 | 5/2014 | Williams |
| 2014/0144968 A1 | 5/2014 | Shelton, IV |
| 2014/0144969 A1 | 5/2014 | Scheib et al. |
| 2014/0151429 A1 | 6/2014 | Scheib et al. |
| 2014/0151430 A1 | 6/2014 | Scheib et al. |
| 2014/0158744 A1 | 6/2014 | Patel et al. |
| 2014/0158745 A1 | 6/2014 | Milliman |
| 2014/0158747 A1 | 6/2014 | Measamer et al. |
| 2014/0166717 A1 | 6/2014 | Swayze et al. |
| 2014/0166718 A1 | 6/2014 | Swayze et al. |
| 2014/0166719 A1 | 6/2014 | Bettuchi et al. |
| 2014/0166727 A1 | 6/2014 | Swayze et al. |
| 2014/0166728 A1 | 6/2014 | Swayze et al. |
| 2014/0175149 A1 | 6/2014 | Smith et al. |
| 2014/0191011 A1 | 7/2014 | Williams |
| 2014/0191012 A1 | 7/2014 | Chen et al. |
| 2014/0197224 A1 | 7/2014 | Penna |
| 2014/0197225 A1 | 7/2014 | Penna |
| 2014/0217144 A1 | 8/2014 | Milliman |
| 2014/0217147 A1 | 8/2014 | Milliman |
| 2014/0217148 A1 | 8/2014 | Penna |
| 2014/0231488 A1 | 8/2014 | Holsten et al. |
| 2014/0239046 A1 | 8/2014 | Milliman |
| 2014/0252062 A1 | 9/2014 | Mozdzierz |
| 2014/0263547 A1 | 9/2014 | Tanner et al. |
| 2014/0263556 A1 | 9/2014 | Mozdzierz et al. |
| 2014/0263563 A1 | 9/2014 | Stokes et al. |
| 2014/0263573 A1 | 9/2014 | Jankowski et al. |
| 2014/0284370 A1 | 9/2014 | Sahin |
| 2014/0284373 A1 | 9/2014 | Shelton, IV et al. |
| 2014/0291377 A1 | 10/2014 | Sahin |
| 2014/0326777 A1 | 11/2014 | Zingman |
| 2014/0332579 A1 | 11/2014 | Nalagatla et al. |
| 2014/0353355 A1 | 12/2014 | Milliman |
| 2014/0358167 A1 | 12/2014 | Armstrong |
| 2014/0367444 A1 | 12/2014 | Williams |
| 2014/0367450 A1 | 12/2014 | Williams |
| 2015/0001275 A1 | 1/2015 | Holsten et al. |
| 2015/0014392 A1 | 1/2015 | Williams et al. |
| 2015/0014393 A1 | 1/2015 | Milliman |
| 2015/0028079 A1 | 1/2015 | Rebuffat et al. |
| 2015/0041519 A1 | 2/2015 | Williams |
| 2015/0048140 A1 | 2/2015 | Penna et al. |
| 2015/0053747 A1 | 2/2015 | Prior |
| 2015/0060523 A1 | 3/2015 | Patel et al. |
| 2015/0060524 A1 | 3/2015 | Kostrzewski |
| 2015/0060525 A1 | 3/2015 | Vestweber |
| 2015/0069108 A1 | 3/2015 | Williams |
| 2015/0083772 A1 | 3/2015 | Miller et al. |
| 2015/0083773 A1 | 3/2015 | Measamer et al. |
| 2015/0083774 A1 | 3/2015 | Measamer et al. |
| 2015/0083775 A1 | 3/2015 | Leimbach et al. |
| 2015/0083778 A1 | 3/2015 | Li et al. |
| 2015/0083779 A1 | 3/2015 | Li et al. |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2524656 A2 | 11/2012 |
| EP | 2873380 A1 | 5/2015 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 2001/054594 A1 | 8/2001 |
| WO | 2008/107918 A1 | 9/2008 |

* cited by examiner

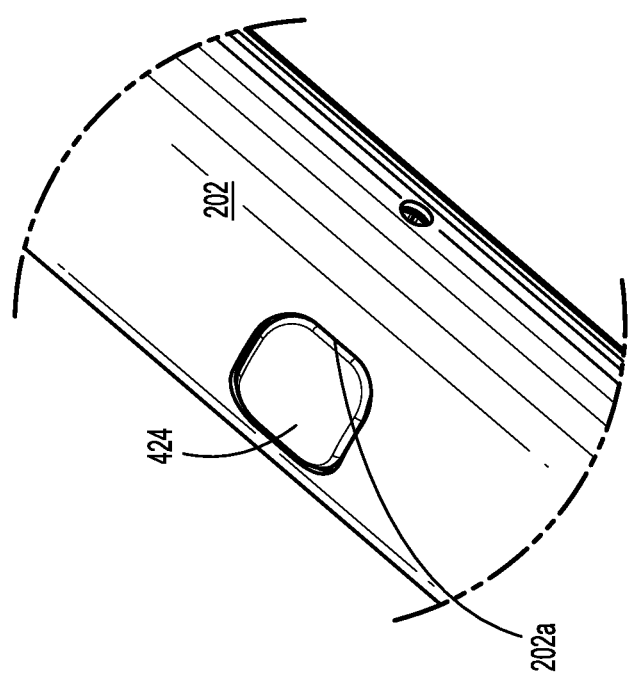
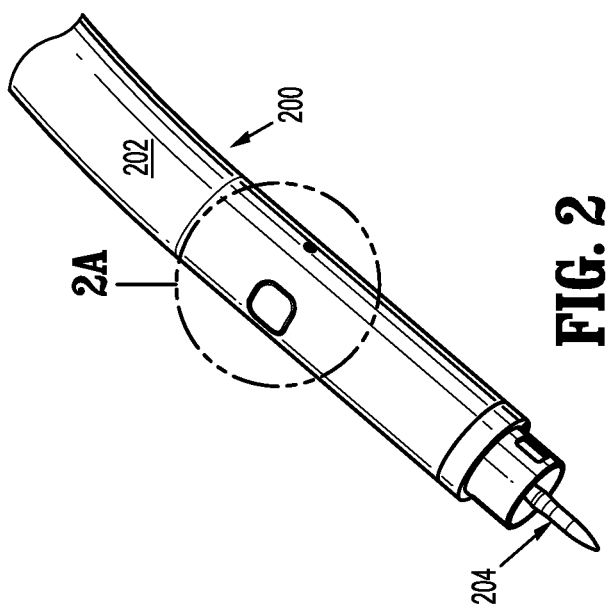

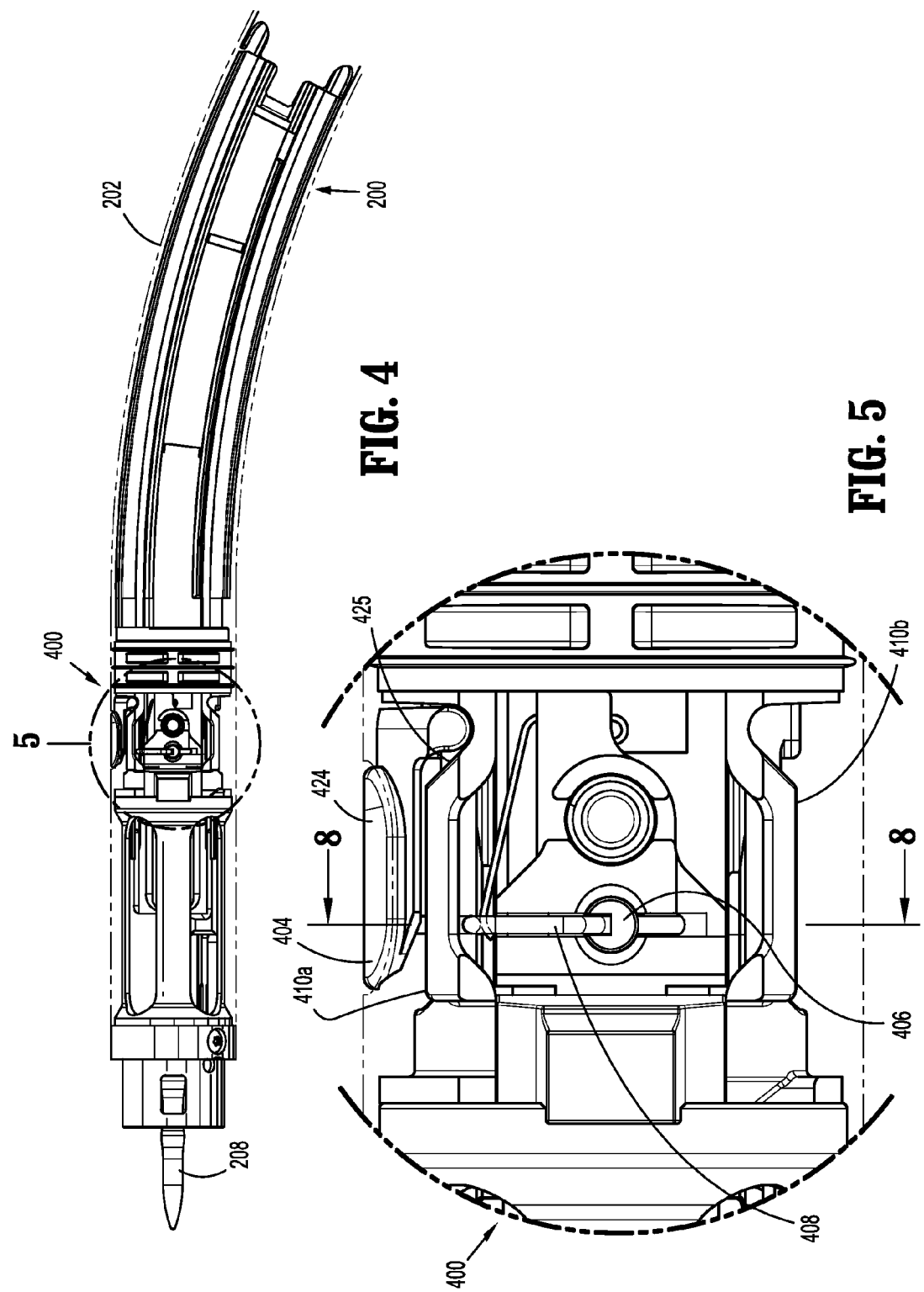

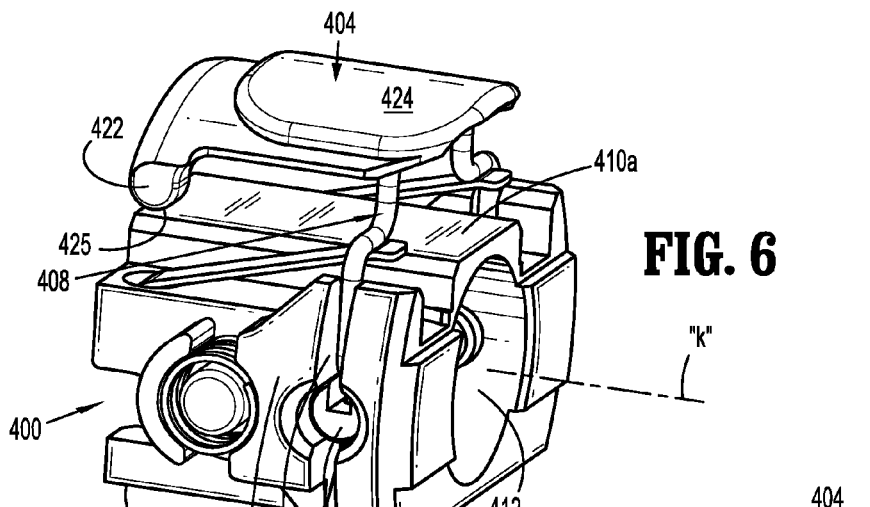
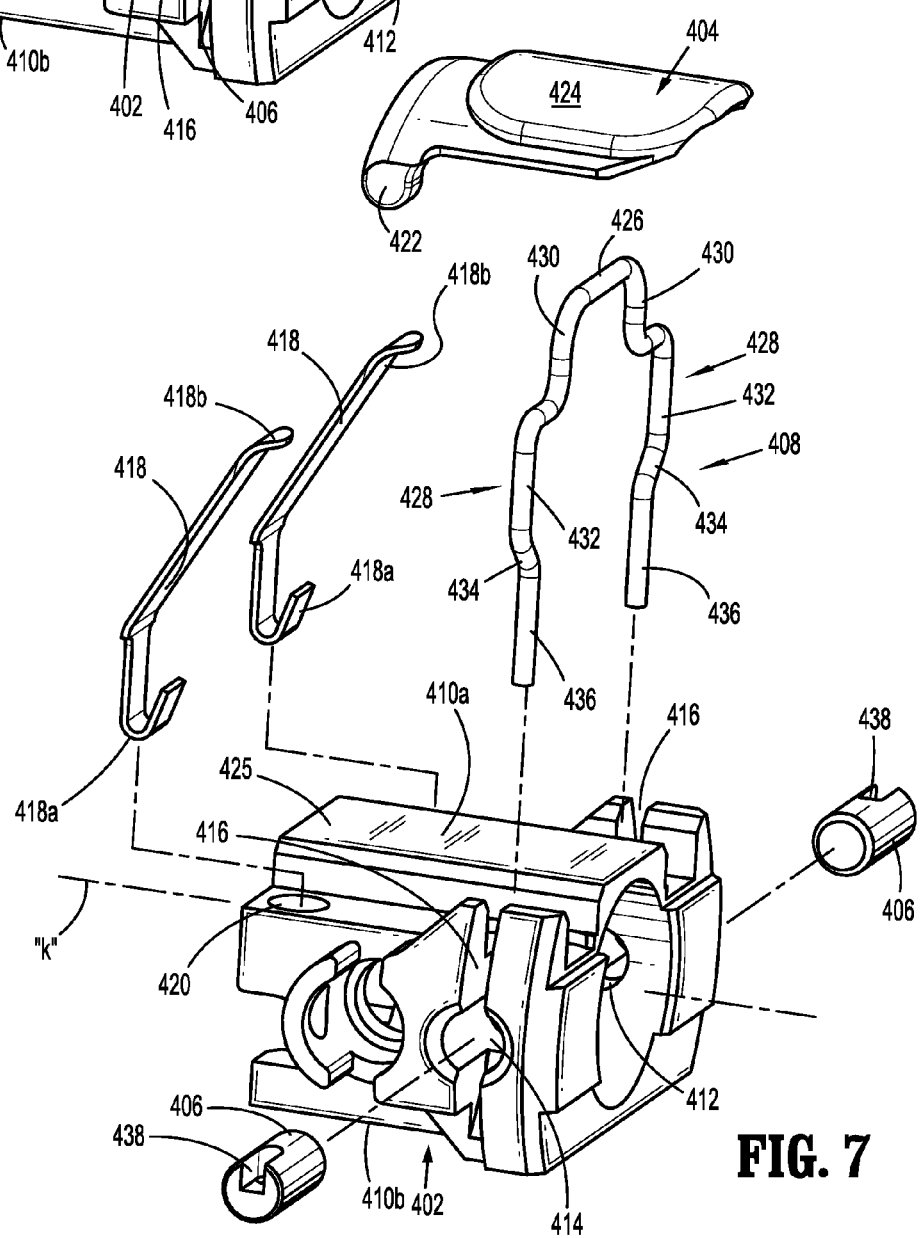

SURGICAL ANASTOMOSIS APPARATUS

BACKGROUND

1. Technical Field

The present disclosure relates to a surgical fastener instrument for applying surgical fasteners to body tissue and, more particularly, relates to a surgical circular fastener instrument incorporating a mechanism to permit selective mounting and release of an anvil retainer and/or anvil relative to the fastener head of the instrument.

2. Description of Related Art

Anastomosis refers to the surgical joining of separate hollow tissue sections. Typically, an anastomosis procedure follows surgery in which a diseased or defective section of a hollow tissue or organ structure is removed, thus requiring the joining of the remaining end sections of the tissue. Depending on the particular procedure performed and/or other factors, the end sections of the tissue may be joined by circular anastomosis, e.g., end-to-end anastomosis, end-to-side anastomosis, or side-to-side anastomosis.

In a circular anastomosis procedure, a fastener instrument drives a circular array of fasteners or staples through each of two end sections of tissue to join the end sections in end-to-end relation, and simultaneously core any tissue within the newly joined sections to clear a passage therethrough. A conventional circular anastomosis instrument includes a handle, an elongated shaft and a fastener head or cartridge at the end of the elongated shaft. An anvil assembly including an anvil rod and an attached anvil head is mountable relative to the fastener cartridge. The tissue end sections are clamped between the anvil head and the fastener cartridge, and the instrument is actuated causing fasteners to be driven through the tissue end sections for crimping by the anvil head.

SUMMARY

Accordingly, the present disclosure is directed to further improvements in end to end or circular anastomosis instruments, particularly, with instruments intended to be reused and sterilized in whole or in part. In one embodiment, a surgical circular fastener apparatus includes an elongated body defining a longitudinal axis and having proximal and distal ends, a fastener cartridge disposed adjacent the distal end of the body, an anvil retainer or trocar releasably mounted relative to the fastener cartridge and a manually operably release configured to move between a first position corresponding to a secured condition of the anvil retainer relative to the fastener cartridge and a second position corresponding to a release condition of the anvil retainer relative to the fastener cartridge. The anvil retainer or trocar may be couplable to an anvil assembly.

In embodiments, the elongated body includes a release housing with the manually operable release being mounted for movement relative to the release housing. The release housing may include at least one lock. The at least one lock may be operatively coupled to the manually operable release and configured to move between a locked position in secured engagement with the anvil retainer to prevent removal of the anvil retainer relative to the fastener cartridge upon movement of the manually operable release to the first position, and an unlocked position released from the anvil retainer to permit removal or mounting of the anvil retainer relative to the fastener cartridge upon movement of the manually operable release to the second position.

In some aspects, the release housing includes a lock drive. The lock drive may be coupled to the manually operable release and configured to position the at least one lock in the locked position upon movement of the manually operable release to the first position and configured to position the at least one lock in the unlocked position upon movement of the manually operable release to the second position.

In certain embodiments, the release housing has at least one lock bore with the at least one lock being dimensioned and adapted to traverse the lock bore during movement between the locked position and the unlocked position. The release housing may define first and second lock bores and have first and second locks respectively disposed within the first and second lock bores. The first and second locks traverse respective first and second lock bores during movement between the locked position and the unlocked position.

The manually operable release may be normally biased toward the first position.

In embodiments, the lock drive is dimensioned and adapted to move within the release housing between an unactuated position corresponding to the first position of the manually operable release and an actuated position corresponding to the second position of the manually operable release. A spring may be configured to engage the lock drive to bias the lock drive to the unactuated position and the manually operable release to the first position. The lock drive may be slidably mounted within the release housing between the unactuated position and the actuated position. In one aspect, the lock drive includes at least one cam segment dimensioned and configured to move the at least one lock to the locked position upon movement of the lock drive to the unactuated position and the manually operable release to the first position, and dimensioned and configured to move the at least one lock in a radial outward direction to the unlocked position released from the anvil retainer upon movement of the lock drive to the actuated position and the manually operable release to the second position.

In certain embodiments, the anvil retainer defines a lock opening whereby the at least one lock is dimensioned and configured to be at least partially received within the lock opening upon movement to the locked position and released from the lock opening upon movement to the unlocked position.

The present disclosure also relates to a surgical circular fastener apparatus including an elongated body defining a longitudinal axis and having leading and trailing ends, a fastener cartridge disposed adjacent the distal end of the elongated body, an anvil retainer or trocar releasably mounted relative to the fastener cartridge and defining at least one lock recess, and an anvil retainer release mechanism for selectively securing and releasing the anvil retainer relative to the fastener cartridge. The release mechanism includes a release housing, a manually operably release mounted to the release housing and configured to move between a first position and a second position, and at least one lock operably coupled to the manually operable release. The at least one lock is mounted for movement within the release housing between a locked position and an unlocked position upon movement of the manually operable release between respective first and second positions thereof. The at least one lock is configured to be received within the at least one lock recess of the anvil retainer to secure the anvil retainer relative to the fastener cartridge when in the locked position, and configured to be released from the at least one lock recess to release the anvil retainer to permit mounting or release of the anvil retainer relative to the fastener cartridge when in the unlocked position. In embodiments, the anvil retainer release mechanism includes a pair of locks and the anvil retainer defines a pair of lock recesses.

In aspects, the release mechanism includes a lock drive coupled to the manually operable release and movable within the retainer housing during movement of the manually operable release between the first and second positions. The lock drive may define cam segments dimensioned to engage and position the locks in respective locked and unlocked positions thereof. The manually operable release may be normally biased toward the first position.

The anvil release mechanism of the present disclosure permits removal of the anvil retainer or trocar, with or without the mounted anvil, during or subsequent to the surgical procedure thereby facilitating replacement of a new or sterilized retainer and/or anvil for immediate reuse. The release mechanism may be operated with a single button or manually operable member to release the anvil retainer or trocar. Reinsertion of the anvil retainer or trocar may be readily effected through activation of the single button.

Other advantages of the present disclosure will be appreciated from the following description.

BRIEF DESCRIPTION OF THE DRAWINGS

Embodiments of the present disclosure will be appreciated by reference to the accompanying drawings wherein:

FIG. 2 is a perspective view illustrating the distal end of the elongated tool with the end effector removed;

FIG. 2A is an enlarged isolated view of the area of detail identified in FIG. 2;

FIG. 4 is a side elevation view of the elongated tool with the outer shell removed;

FIG. 5 is an enlarged isolated view of the area of detail identified in FIG. 4 illustrating the retainer release mechanism for releasably securing the anvil retainer relative to the elongated tool;

FIG. 6 is a perspective view of the retainer release mechanism;

FIG. 7 is an exploded perspective view of the retainer release mechanism;

DETAILED DESCRIPTION

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

Figure 1:
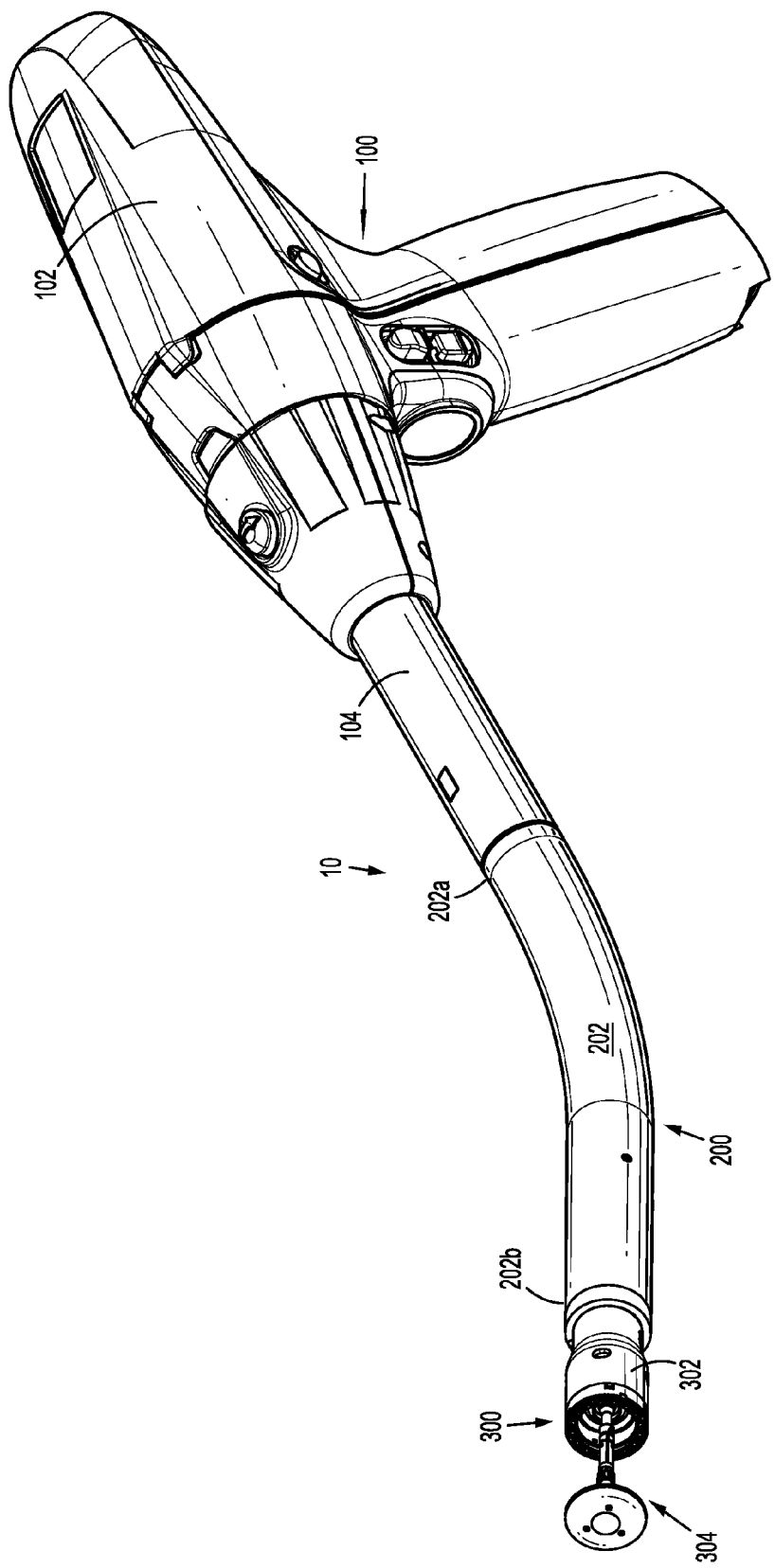
FIG. 1 is a perspective view of a surgical anastomosis apparatus for applying an annular or circular array of fasteners in accordance with the principles of the present disclosure illustrating the handle, the elongate tool and an end effector mounted to the elongated tool.

Referring now to the drawings where like reference numerals indicate similar components throughout the several views, FIG. 1 illustrates the surgical fastener apparatus 10 in accordance with the principles of the present disclosure. The surgical fastener apparatus 10 may be adapted to apply an annular or circular array of fasteners or staples to tissue in connection with an end-to-end or circular anastomosis of tissue. The surgical fastener apparatus 10 includes a handle 100 and an elongated tool 200 connectable to the handle 100. The handle 100 may be any handle assembly having at least one actuator, and in some embodiments, two or more actuators adapted to control operation of the fastener apparatus 10. The handle 100 may be powered incorporating a motor and supporting circuitry to operate the apparatus 10. The handle 100 may include a handle frame 102 and a handle shaft 104 extending from the handle frame 102. The elongated tool 200 is couplable to the handle shaft 104. In the alternative, the handle 100 may be devoid of the handle shaft 104 whereby the tool 200 is directly connected to the handle frame 102. It is contemplated that the handle 100 may be reusable.

The elongated tool 200 may be a single use loading unit (SULU) or a multi-use loading unit (MULU) having an end effector 300 adapted, e.g., for single or multiple firing of one or more fasteners. All or a portion of the elongated tool 200 and the end effector 300 may be reusable with the reusable components subject to sterilization procedures after use.

The end effector 300 may be a fastener firing effector, which in one embodiment, includes a staple or fastener cartridge 302 and an anvil 304. The fastener cartridge 302 may be mounted to, or a component of, the elongated tool 200, and houses a plurality of fasteners. In the alternative, the fastener cartridge 302 may be releasably mounted to the elongated tool 200, and replaced with another fastener cartridge 302 upon exhaustion of the supply of fasteners. The anvil 304 is releasably mountable relative to the fastener cartridge 302. When coupled to the elongated tool 200, the anvil 304 is movable relative to the fastener cartridge 302 between open and approximated positions. The fasteners are driven from the fastener cartridge 302 through tissue positioned about the components, and crimped by the anvil 304. Further details of the end effector 300 will be discussed in greater detail hereinbelow.

Figure 3:
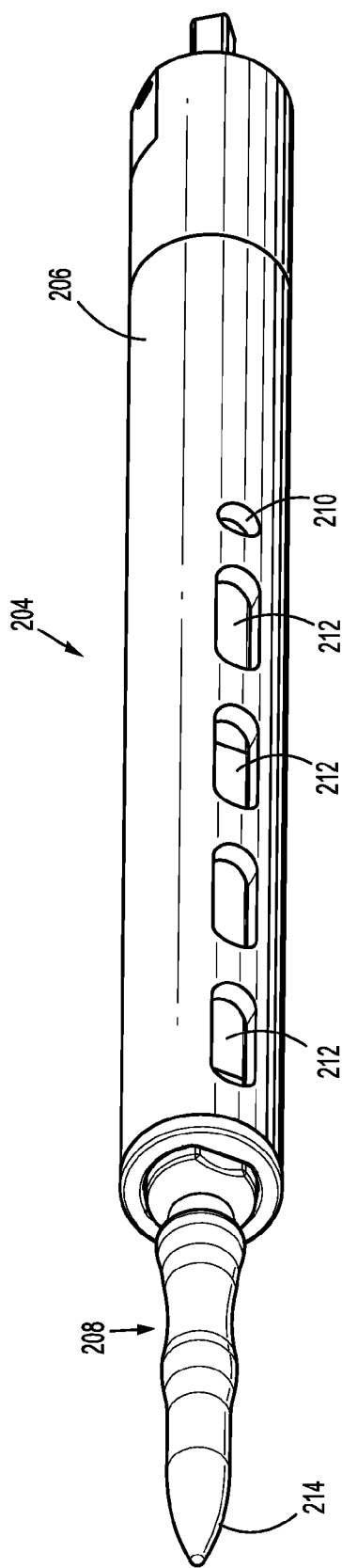
FIG. 3 is a perspective view of an anvil retainer or trocar for mounting an anvil of the end effector to the elongated tool, illustrating the retainer sleeve and the retainer shaft at least partially disposed within the retainer sleeve.

Referring now to FIGS. 2-3, the elongated tool 200 includes an outer body or shell 202 which houses the components of the fastener firing mechanism for firing the fasteners and the components of the approximating mechanism for approximating the anvil 304 and the fastener cartridge 302. The outer body 202 defines proximal or trailing and distal or leading ends 202a, 202b. The elongated tool 200 further includes an anvil retainer or trocar 204 which is releasably mounted to the outer body 202 and relative to the fastener cartridge 302. In FIG. 2, the fastener cartridge 302 is shown removed (for illustrative purposes) from the outer body 202 of the elongated tool 200. The anvil retainer 204 (only a portion of which is shown in FIG. 2) secures and/or mounts the anvil 304 relative to the fastener cartridge 302, and may function as a trocar assisting in advancing the elongated tool 200 through tissue in the absence of the mounted anvil 304.

As best depicted in FIG. 3, the anvil retainer 204 includes a retainer sleeve 206 and an anvil retainer shaft 208 releasably mounted to the sleeve 206. The sleeve 206 includes at least one mounting hole 210 extending at least partially or completely through the wall of the sleeve 206. In one embodiment, the sleeve 206 includes a pair of diametrically opposed mounting holes 210 disposed at the same axial location (only one mounting hole 210 is shown in FIG. 3). The mounting holes 210 may be circular in dimension although other configurations are envisioned as well. The sleeve 206 may include one or more relief holes 212, or optionally, be devoid of the relief holes 212. The relief holes 212 may permit a degree of expansion of the outer sleeve 206 to facilitate insertion and/or retention of the retainer shaft 208 within the sleeve 206 or may engage cooperating structure of the retainer shaft 208 to assist in securing the retainer shaft 208 within the sleeve 206.

The retainer shaft 208 may be releasably secured within the sleeve 206 through conventional arrangements such as a friction fit, bayonet coupling, detent mechanism or the like. The retainer shaft 208 may include a distal trocar tip 214 having a tapered configuration to facilitate passage through tissue to assist the anvil retainer 204 in functioning like a trocar. The retainer shaft 208 is dimensioned to couple with corresponding structure of the anvil 304 to releasably couple the anvil 304 to the anvil retainer 204. In the alternative, the sleeve 206 and the retainer shaft 208 may be secured to each other in fixed relation therewith.

Referring now to FIGS. 4-7, the anvil retainer release mechanism 400 for releasably mounting the anvil retainer 204 relative to the outer body 202 of the elongated tool 200 will be discussed. The release mechanism 400 is mounted to the outer body 202 of the elongated tool 200 proximal of the end effector 300. In FIG. 4, the end effector 300 is not shown. Any conventional means for securing the release mechanism 400 to, or within, the outer body 202 are envisioned including mechanical arrangements, adhesives or the like. As best depicted in FIGS. 6-7, the release mechanism 400 includes a release housing 402 defining a housing axis "k", a manually operable release 404, a pair of locks 406 and a lock drive 408. The manually operable release 404, the locks 406 and the lock drive 408 are each mounted for movement within and relative to the release housing 402. In one embodiment, the release housing 402 includes upper and lower surfaces 410a, 410b, a central axial bore 412 for reception of the anvil retainer 204, first and second lock receiving bores 414 orthogonal to the housing axis "k" for receiving respective locks 406, and first and second channels 416 for at least partially receiving the lock drive 408. The release mechanism 400 further may include a pair of springs 418, e.g., leaf springs, having one end 418a secured within openings 420 of the release housing 402 and the other free ends 418b in engagement with the lock drive 408 as will be discussed hereinbelow.

With continued reference to FIGS. 4-7, the manually operable release 404 includes at least one cylindrical hinge or pivot 422 (e.g., two spaced hinges 422) and a manually engagement segment 424 extending from the pivot hinges 422. The hinges 422 rotate within recess(es) 425 (FIG. 5) within the upper surface 410a of the release housing 402 during movement of the manually operable release 404 between first and second position thereof. Alternatively, a recess accommodating the hinges 422 may be associated with the outer body 202. In FIGS. 4-6, the manually operable release 404 is in the first position which may correspond to a secured condition of the anvil retainer 204 relative to the elongated tool 200 and/or the fastener cartridge 302. The manual engagement segment 424 of the manually operable release 404 is accessible through a window 202a in the outer body 202 of the elongated tool 200, as depicted in FIG. 2A, for access by the clinician.

Figure 8:
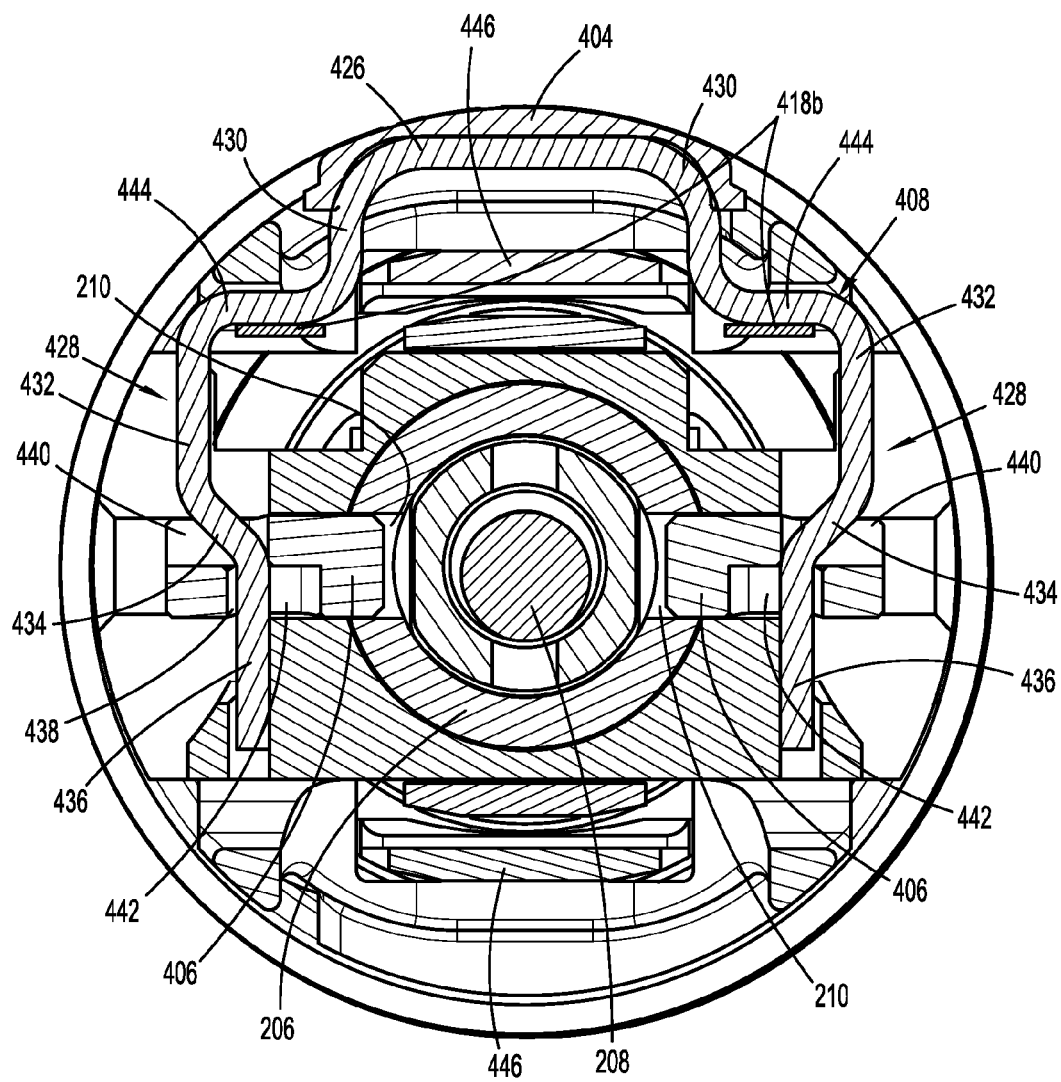
FIG. 8 is a cross-sectional view of the retainer release mechanism taken along the lines 8-8 of FIG. 5 illustrating the relationship of the manually operable release, the lock drive and the locks relative to the anvil retainer when the manually operable member is in a first position corresponding to a secured condition of the anvil retainer relative to the elongated tool.

With reference to FIGS. 5-7, in conjunction with the cross-sectional view of FIG. 8, the lock drive 408 depends downwardly or radially inwardly relative to the housing axis "k" from the manually operable release 404, and may or may not be secured to the manually operable release 404. As best depicted in FIGS. 7-8, the lock drive 408 includes a central beam 426 and two legs 428 extending from the central beam 426. The central beam 426 engages the manually engagement segment 424 of the manually operable release 404. The two legs 428 of the lock drive 408 include opposed leg segments 430 extending continuously from the central beam 426, leading to a pair of recessed or outward segments 432 disposed radially outwardly of the central beam 426. The legs 428 of the lock drive 408 further define a pair of inwardly tapered or cam segments 434 depending contiguously from the outward segments 432 and leading to lower leg segments 436.

With continued reference to FIGS. 7-8, the locks 406 of the release mechanism 400 each define passages 438 extending through the approximate midsection of the respective locks 406, and also define upper and lower relief areas 440, 442 communicating with the passages 438. The passages 438 at least partially receive the legs 428 (e.g., at least the lower leg segments 436) of the lock drive 408. In the first position of the manually operable release 404 corresponding to the locked position of the locks 406 with respect to the anvil retainer 204, the lower leg segments 436 are disposed within the passages 438 to position the locks 406 within the mounting holes 210 of the sleeve 206 of the anvil retainer 204 (FIG. 8). This corresponds to the secured condition of the anvil 204 relative to the fastener cartridge 302 and/or the elongated tool 200. The manually operable release 404 is normally biased to the first condition through the pair of springs 418 with the free ends 418b engaging the shelves 444 of the lock drive 408, thereby driving the lock drive 408 to the upward or unactuated position and the manually operable release 404 to the first position of FIG. 8.

FIG. 8 also depicts a pair of pushers 446 which extend through the release housing 402 (e.g., may ride along the upper and lower surfaces 410a, 410b) and couple with the fastener firing mechanism extending through the elongated tool 200 and with the fastener cartridge 302, and a pair of approximator shafts 448 which couple either with the anvil retainer 204 and/or the anvil 304 to move the anvil 304 between open and approximated conditions relative to the fastener cartridge 302. The approximator shafts 448 may extend between the spaced hinges 422 of the manually operable release 404.

Figure 9:
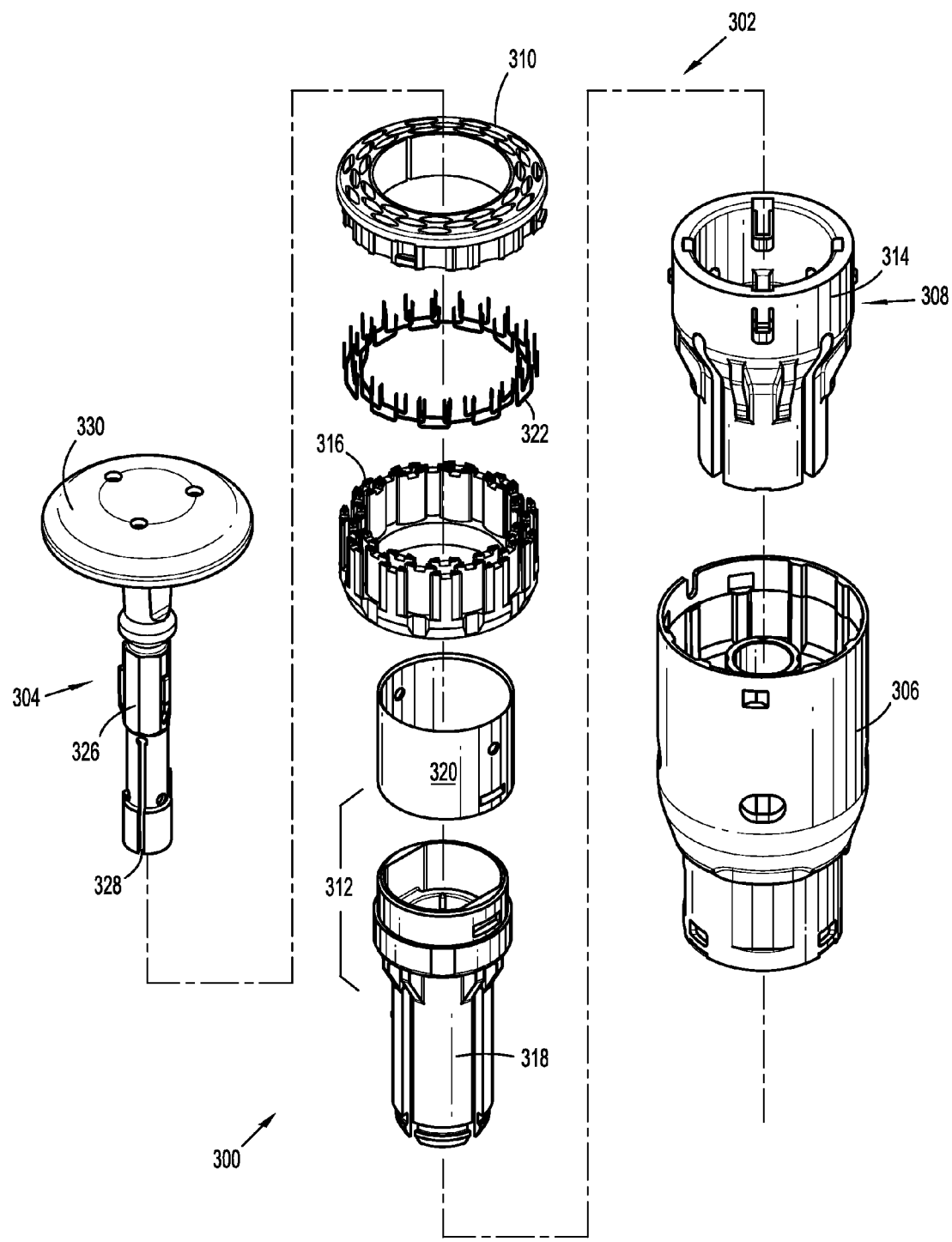
FIG. 9 is an exploded perspective view of the end effector including a fastener cartridge and an anvil.

Referring now to FIG. 9, one exemplative end effector 300 for use with the elongated tool 200 is illustrated. Features of the end effector 300 are disclosed in commonly assigned U.S. Patent Publication No. 2015/0014393 to Milliman, the entire contents of which are incorporated by reference herein. The fastener cartridge 302 of the end effector 300 includes a housing 306, a pusher assembly 308, a fastener cartridge 310, and a knife assembly 312. The pusher assembly 308 includes a pusher adapter 314 and a pusher member 316, which couples with the pair of pushers 446 (FIG. 8) extending within the outer body 202 of the elongated tool 200. The knife assembly 312 includes a knife carrier 318 and a circular knife 320, which may be operatively coupled to the pushers 446. The fastener cartridge 310 includes a plurality of fasteners or staples 322 mounted within recesses 324 of the fastener cartridge 310.

With continued reference to FIG. 9, the anvil 304 of the end effector 300 includes an anvil shaft 326 which defines a longitudinal bore 328 for at least partial reception of the retainer shaft 208 of the anvil retainer 204. When positioned within the longitudinal bore 328, the retainer shaft 208 and the anvil 304 are coupled to each other. The anvil 304 includes a circular anvil head 330 with pockets (not shown) which receive and crimp the fasteners or staples 322 ejected by the fastener cartridge 310. In embodiments, the anvil 304 and the anvil retainer 204 may be a single component. Thus, mounting and release of the anvil retainer 204 will cause corresponding mounting and release of the anvil 304.

In one exemplary use, the elongated tool 200 with the fastener cartridge 310 and the anvil retainer 204 mounted thereto is advanced within a section of a tubular body organ. As indicated, the distal trocar tip 214 of the retainer shaft 208 may facilitate passage through tissue the organ. The anvil 304 is advanced or positioned in a second section of tubular body organ in opposed relation to the fastener cartridge 310. The ends of the first and second sections of the tubular body organs are secured about the fastener cartridge 310 and the anvil head 330, respectively. The anvil shaft 326 is mounted to the retainer shaft 208, and the anvil 304 and the fastener cartridge 302 are approximated through activation of one of the actuators of the handle frame 102. The pusher assembly 308 is advanced (through, e.g., actuation of the handle 100 and movement of the pushers 446 within the release housing 402) causes advancing movement of the pusher member 316 and the knife assembly 312 to eject the fasteners or staples 322 for crimping against the anvil head 330 and to carve any tissue disposed within the connected organs.

Figure 10:
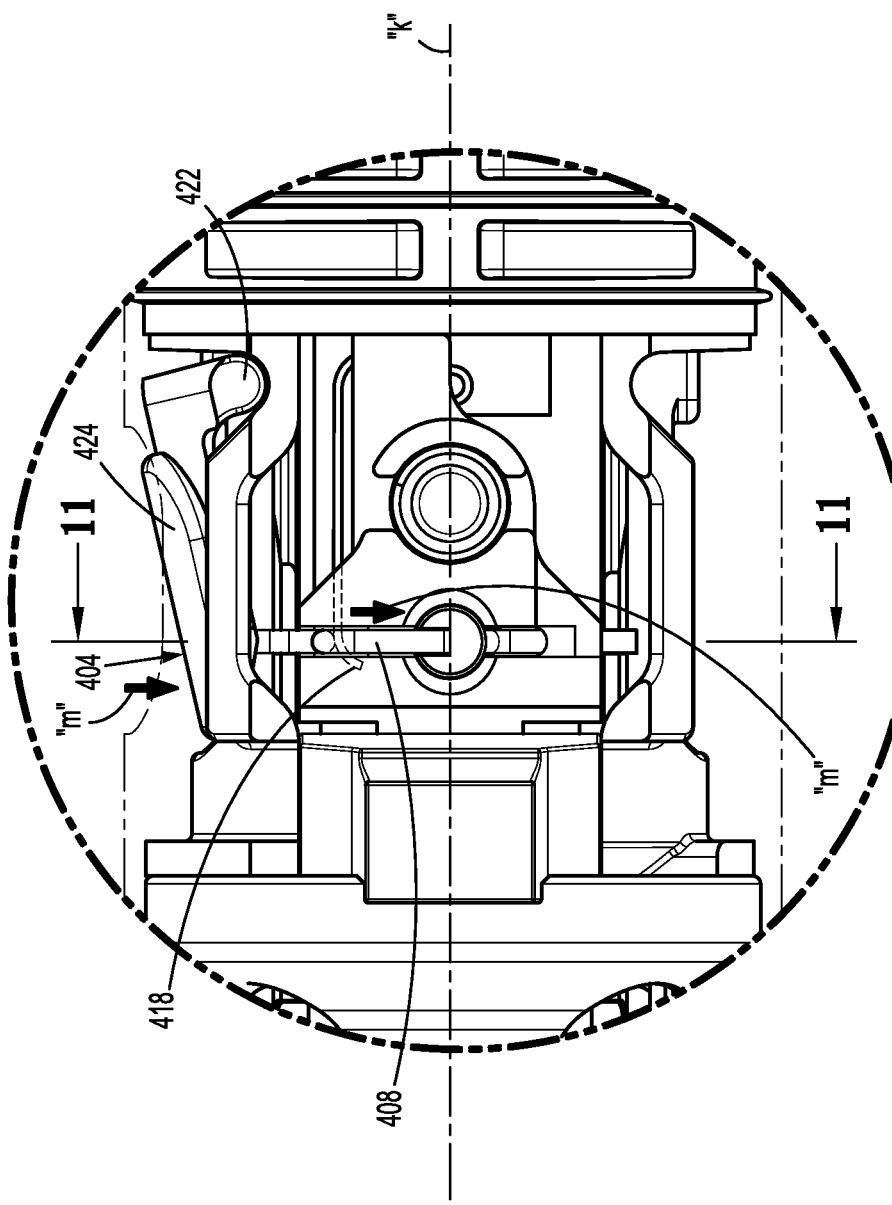
FIG. 10 is an enlarged isolated view similar to the view of FIG. 5 illustrating the manually operable member of the retainer release mechanism in a second position corresponding to a release condition of the anvil retainer relative to the elongated tool.
Figure 11:
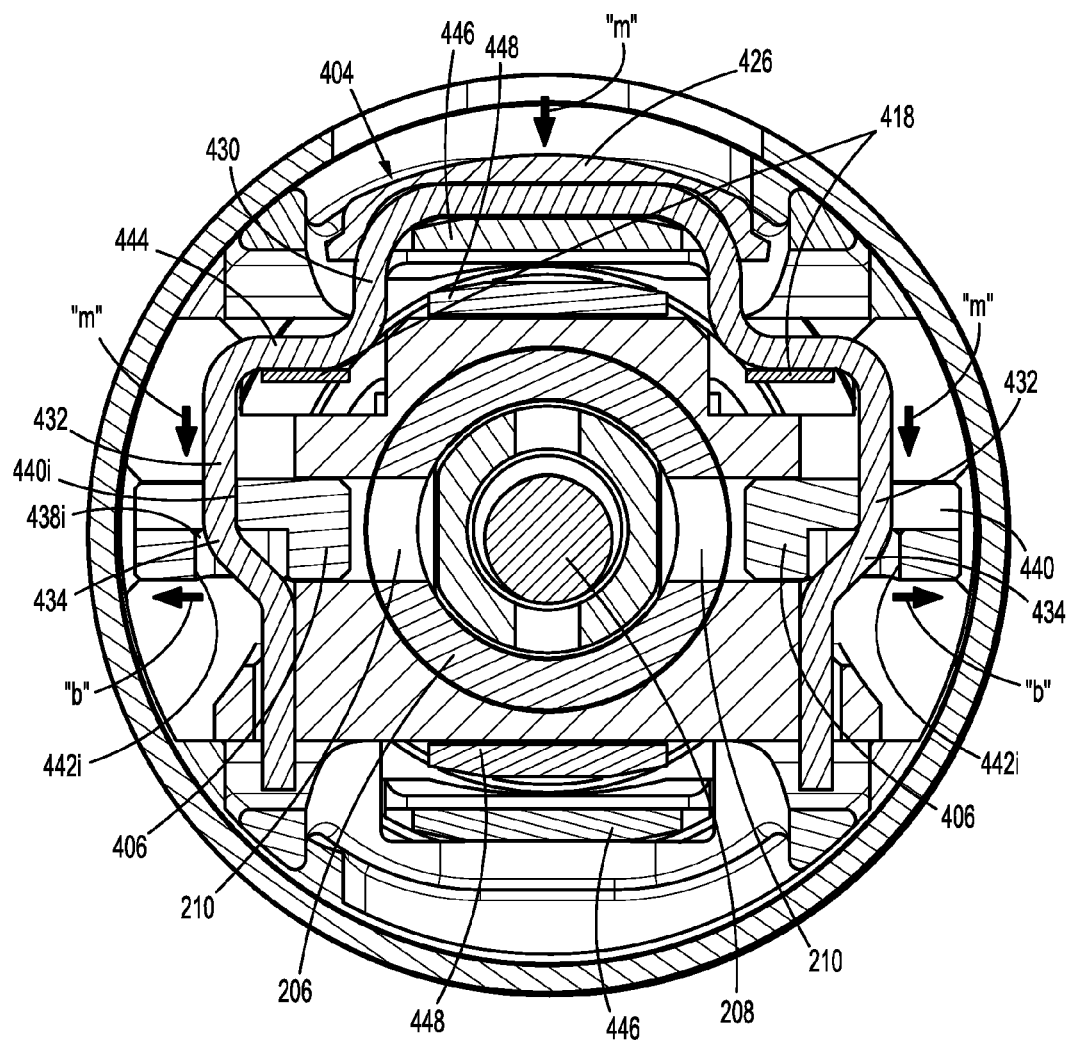
FIG. 11 is a cross-sectional view of the retainer release mechanism taken along the lines 11-11 of FIG. 10 illustrating the relationship of the manually operable release, the lock drive and the locks relative to the anvil retainer when the manually operable member is in the second position.
Figure 12:
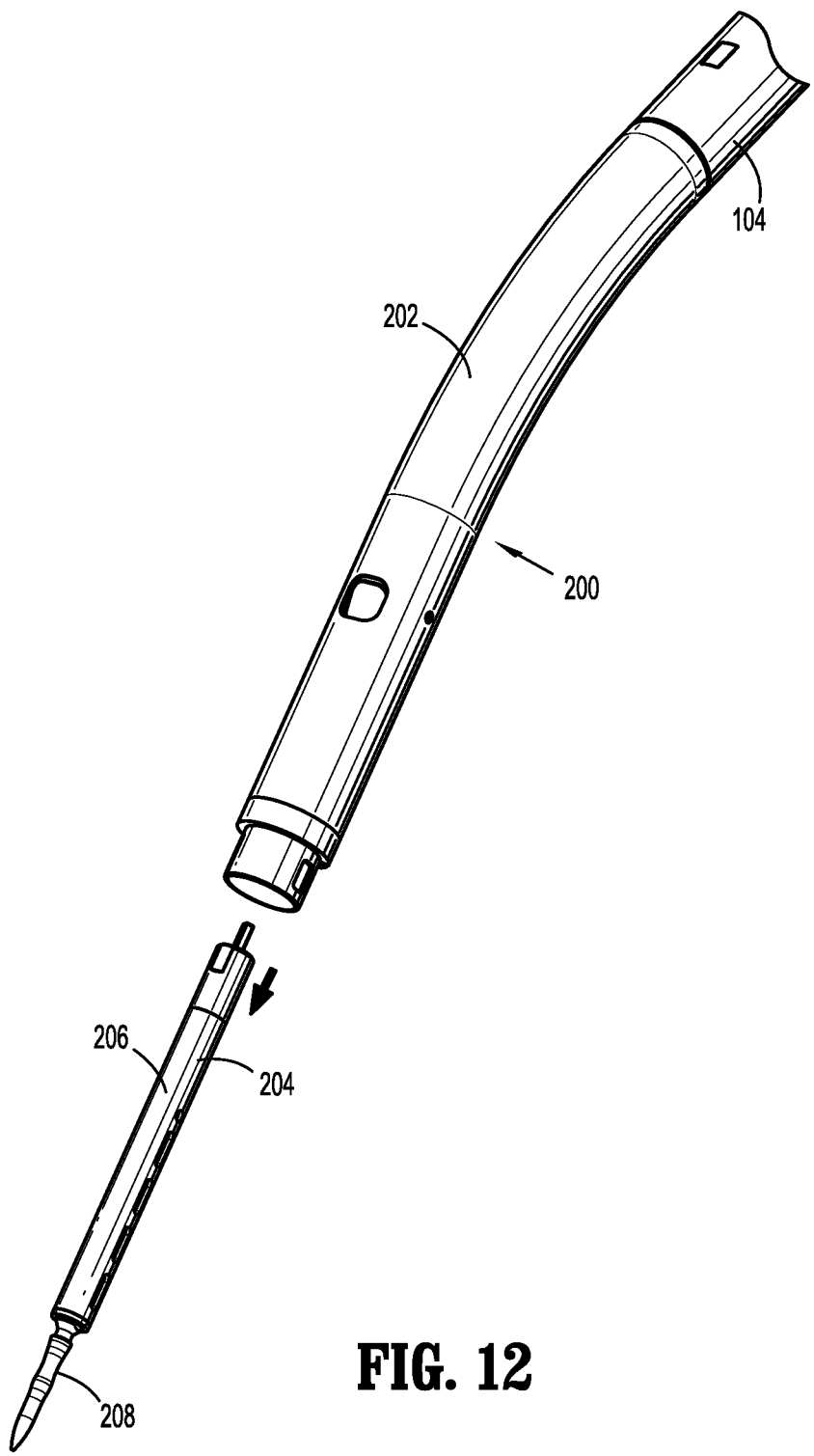
FIG. 12 is a perspective view of the elongated body with the anvil retainer removed through movement of the manually operable release to the second position.

Referring now to FIGS. 10-11, the use of the release mechanism 400 will be described. When it is determined by the clinician that the anvil retainer 204 with or without the mounted anvil 304 is to be released from the outer body 202 of the elongated tool 200, such as, for example, subsequent to the aforedescribed anastomosis procedure, the manually engagement segment 424 of the manually operable release 404 is pushed inwardly relative to axis "k" in the direction "m" to cause it to pivot about the pivot hinges 422 against the bias of the springs 418 and assume the second position thereof corresponding to the release condition of the anvil 204 relative to the fastener cartridge 302 and/or the elongated tool 200. This causes the lock drive 408 to also move in the direction "m" against the bias of the spring 418 to, e.g., its actuated position. During movement of the lock drive 408, the cam segments 434 of the legs 428 traverse the passages 438 of the locks 406, and displace the locks 406 in the radial outward direction (corresponding to directional arrow "b") due to the camming action of the cam segments 434 with at least one of the internal surfaces 440$i$, 442$i$ of the upper and lower relief areas 440, 442 and/or the internal surfaces 438$i$ of the passages 438 of the locks 406. As a result of the radial outward movement of the locks 406, the locks 406 are displaced from the mounting holes 210 of the sleeve 206 (corresponding to the unlocked position of the locks 406) thereby freeing the sleeve 206 and the entire anvil retainer 204 (and the anvil 304 if mounted to the anvil retainer 204) for removal from the elongated tool 200 as depicted in FIG. 12. Thus, removal of the anvil retainer 204 may be effected through simple depression of the manually operable release 404.

Figure 13:
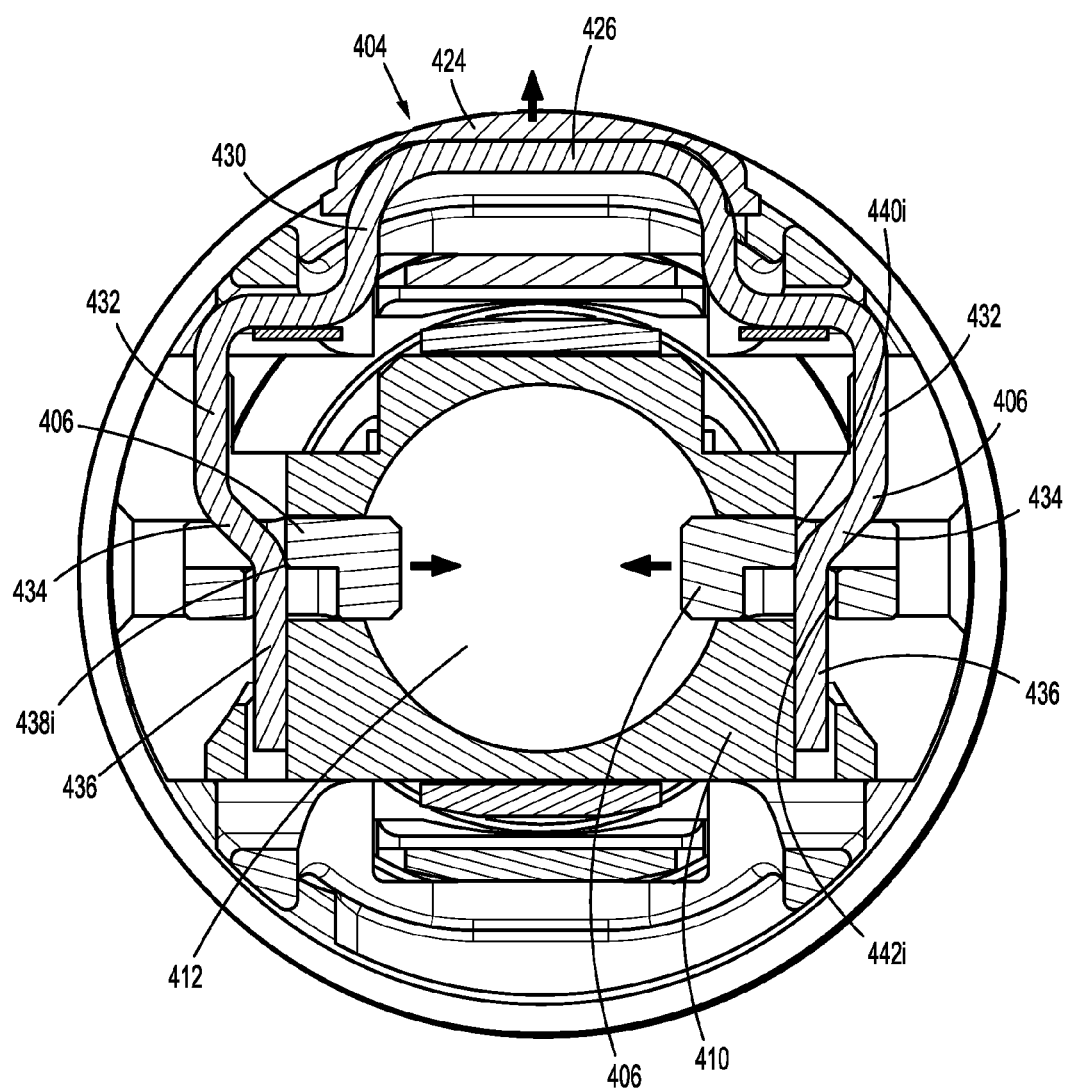
FIG. 13 is a cross-sectional view of the anvil release mechanism illustrating the manually operable release returning to the first position under the influence of the biasing spring.

As depicted in FIG. 13, upon release of the manually operable release 404, the lock drive 408 and the manually operable release 404 return to their respective unactuated and first positions under the influence of the bias of the springs 418 with the cam segments 434 of the lock drive 408 engaging at least one of the internal surfaces 438$i$, 440$i$, 442$i$ defined by the passages 438 and relief areas 440, 442 of the locks 406 thereby positioning the locks 406 in the locked position. To load another anvil retainer 204 (new or sterilized and reused), the manually operable release 404 may be depressed to cause movement to the second position thereof and radial outward displacement of the locks 406 to the unlocked position. The anvil retainer 204 is introduced within the central axial bore 412 of the release housing 402 and the manually operable release 404 is released to assume its second position locks whereby the locks 406 return to the locked position received within the mounting holes 210 of the sleeve 206 of the anvil retainer 204 securing the anvil retainer 204 or trocar relative to the elongated tool 200. An anvil 304 may be introduced within the sleeve 206 prior to, during or after mounting of the anvil retainer 204 to the release housing 402.

The above description and the drawings are provided for the purpose of describing embodiments of the present disclosure and are not intended to limit the scope of the disclosure in any way. For example, although a motorized handle is shown, the present locking apparatus can be provided on a device including a manually operable handle, or a robotic system. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A surgical circular fastener apparatus, which comprises:
an elongated body defining a longitudinal axis and having proximal and distal ends, the elongated body defining a window;
a fastener cartridge disposed adjacent the distal end of the body;
an anvil retainer releasably mounted relative to the fastener cartridge; and
a manually operable release including at least one lock, the manual operable release being accessible through the window and movable between a first position corresponding to a secured condition in which the at least one lock is engaged with the anvil retainer to secure the anvil retainer within the fastener cartridge and a second position in which the at least one lock is disengaged with the anvil retainer to release the anvil retainer from within the fastener cartridge.

2. The surgical fastener apparatus according to claim 1 wherein the elongated body includes a release housing, the manually operable release mounted for movement relative the release housing.

3. The surgical fastener apparatus according to claim 2 wherein the at least one lock is operatively coupled to the manually operable release and configured to move between a locked position in secured engagement with the anvil retainer to prevent removal of the anvil retainer relative to the fastener cartridge upon movement of the manually operable release to the first position, and an unlocked position released from the anvil retainer to permit removal or mounting of the anvil retainer relative to the fastener cartridge upon movement of the manually operable release to the second position.

4. The surgical fastener apparatus according to claim 3 wherein the release housing includes a lock drive, the lock drive coupled to the manually operable release and configured to position the at least one lock in the locked position upon movement of the manually operable release to the first position and configured to position the at least one lock in the unlocked position upon movement of the manually operable release to the second position.

5. The surgical fastener apparatus according to claim 4 wherein the release housing has at least one lock bore, the at least one lock dimensioned and adapted to traverse the lock bore during movement between the locked position and the unlocked position.

6. The surgical fastener apparatus according to claim 5 wherein the release housing defines first and second lock bores and having first and second locks respectively disposed within the first and second lock bores, the first and second locks traversing respective first and second lock bores during movement between the locked position and the unlocked position.

7. The surgical fastener apparatus according to claim 5 wherein the manually operable release is normally biased toward the first position.

8. The surgical fastener apparatus according to claim 7 wherein the lock drive is dimensioned and adapted to move within the release housing between an unactuated position corresponding to the first position of the manually operable release and an actuated position corresponding to the second position of the manually operable release.

9. The surgical fastener apparatus according to claim 8 including a spring configured to engage the lock drive to bias the lock drive to the unactuated position and the manually operable release to the first position.

10. The surgical fastener apparatus according to claim 9 wherein the lock drive is slidably mounted within the release housing between the unactuated position and the actuated position.

11. The surgical fastener apparatus according to claim 10 wherein the lock drive includes at least one cam segment dimensioned and configured to move the at least one lock to the locked position upon movement of the lock drive to the unactuated position and the manually operable release to the first position, and dimensioned and configured to move the at least one lock in a radial outward direction to the unlocked position released from the anvil retainer upon movement of the lock drive to the actuated position and the manually operable release to the second position.

12. The surgical fastener apparatus according to claim 4 wherein the anvil retainer defines a lock opening, the at least one lock dimensioned and configured to be at least partially received within the lock opening upon movement to the locked position and released from the lock opening upon movement to the unlocked position.

13. A surgical circular fastener apparatus, which comprises:
an elongated body defining a longitudinal axis and having leading and trailing ends, the elongated body defining a window;
a fastener cartridge disposed adjacent the distal end of the elongated body;
an anvil retainer releasably mounted relative to the fastener cartridge, the anvil retainer defining at least one lock recess; and
an anvil retainer release mechanism for selectively securing and releasing the anvil retainer relative to the fastener cartridge, the anvil retainer release mechanism including:
a release housing;
a manually operably release accessible through the window, the manually operable release mounted to the retainer housing and configured to move between a first position and a second position; and
at least one lock operably coupled to the manually operable release, the at least one lock mounted for movement within the retainer housing between a locked position and an unlocked position upon movement of the manually operable release between respective first and second positions thereof, the at least one lock configured to be received within the at least one lock recess of the anvil retainer to secure the anvil retainer relative to the fastener cartridge when in the locked position, and configured to be released from the at least one lock recess to release the anvil retainer to permit mounting or release of the anvil retainer relative to the fastener cartridge when in the unlocked position.

14. The surgical fastener apparatus according to claim 13 wherein the anvil retainer release mechanism includes a pair of locks and the anvil retainer defines a pair of lock recesses.

15. The surgical fastener apparatus according to claim 14 wherein the anvil retainer release mechanism includes a lock drive coupled to the manually operable release and movable within the retainer housing during movement of the manually operable release between the first and second positions, the lock drive defining cam segments dimensioned to engage and position the locks in respective locked and unlocked positions thereof.

16. The surgical fastener apparatus according to claim 15 wherein the manually operable release is normally biased toward the first position.

* * * * *